US006524557B1

(12) United States Patent
Bäckström et al.

(10) Patent No.: US 6,524,557 B1

(45) Date of Patent: Feb. 25, 2003

(54) AEROSOL FORMULATIONS OF PEPTIDES AND PROTEINS

(75) Inventors: Kjell Bäckström, Lund (SE); Magnus Dahlbäck, Lund (SE); Ann Johansson, Lund (SE); Göran Källstrand, Bjärred (SE); Elisabet Lindqvist, Lund (SE)

(73) Assignee: AstraZeneca AB, Södertälje (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/624,504

(22) PCT Filed: Dec. 19, 1994

(86) PCT No.: PCT/SE95/01540

§ 371 (c)(1), (2), (4) Date: Apr. 4, 1996

(87) PCT Pub. No.: WO96/19197

PCT Pub. Date: Jun. 27, 1996

(30) Foreign Application Priority Data

Dec. 22, 1994 (SE) ............................................. 9404467
Jul. 6, 1995 (SE) ............................................. 9502453

(51) Int. Cl.[7] .................................................. A61K 9/12

(52) U.S. Cl. ........................................... 424/46; 424/45

(58) Field of Search ........................... 424/45, 46, 489; 514/2

(56) References Cited

U.S. PATENT DOCUMENTS

| | | | | | |
|---|---|---|---|---|---|
| 2,992,645 | A | * | 7/1961 | Fowler | 128/203.15 |
| 3,014,844 | A | | 12/1961 | Thiel et al. | 167/82 |
| 3,632,743 | A | | 1/1972 | Geller et al. | 424/45 |
| 3,671,625 | A | * | 6/1972 | Altounyan | |
| 4,232,002 | A | | 11/1980 | Nogrady | 424/45 |
| 4,462,983 | A | * | 7/1984 | Azria | |
| 4,524,769 | A | * | 6/1985 | Wetterlin | 128/203.15 |
| 4,534,345 | A | * | 8/1985 | Wetterlin | 128/203.15 |
| 4,537,772 | A | * | 8/1985 | Alexander | 514/9 |
| 4,548,922 | A | | 10/1985 | Carey et al. | 514/4 |
| 4,613,500 | A | | 9/1986 | Suzuki et al. | 429/85 |
| 4,668,218 | A | * | 5/1987 | Virtanen | 604/58 |
| 4,690,952 | A | | 9/1987 | Kagatani et al. | 514/808 |
| 4,731,360 | A | * | 3/1988 | Alexander | 514/201 |
| 4,746,508 | A | | 5/1988 | Carey et al. | 424/88 |
| 4,788,221 | A | | 11/1988 | Kagati et al. | 514/808 |
| 4,794,000 | A | | 12/1988 | Ecanow | 424/457 |
| 4,847,298 | A | | 7/1989 | Alexander et al. | 514/565 |
| 4,849,405 | A | | 7/1989 | Ecanow | 514/3 |
| 4,895,719 | A | | 1/1990 | Radhakrishnan et al. | 424/45 |
| 4,900,730 | A | | 2/1990 | Miyauchi | 514/12 |
| 4,907,583 | A | * | 3/1990 | Wetterlin et al. | 128/203.15 |
| 4,926,852 | A | * | 5/1990 | Zoltan et al. | 128/200.23 |
| 4,959,358 | A | | 9/1990 | Carey et al. | 514/171 |
| 4,963,367 | A | | 10/1990 | Ecanow | 424/485 |
| 4,994,439 | A | | 2/1991 | Longenecker et al. | 514/3 |
| 5,006,343 | A | | 4/1991 | Benson et al. | 424/450 |
| 5,011,678 | A | | 4/1991 | Wang et al. | 424/45 |
| 5,118,494 | A | | 6/1992 | Schultz et al. | 424/45 |
| 5,122,127 | A | * | 6/1992 | Stanley | 604/890.1 |
| 5,122,376 | A | | 6/1992 | Aliverti et al. | 424/405 |
| 5,126,123 | A | * | 6/1992 | Johnson | |
| 5,145,684 | A | * | 9/1992 | Liversidge et al. | 424/45 |
| 5,179,079 | A | | 1/1993 | Hansen et al. | 514/4 |
| 5,192,548 | A | * | 3/1993 | Velasquez et al. | 424/443 |
| 5,200,393 | A | | 4/1993 | Weiner | 514/3 |
| 5,202,129 | A | | 4/1993 | Samejima et al. | 424/489 |
| 5,204,108 | A | | 4/1993 | Illum | 424/434 |
| 5,225,183 | A | * | 7/1993 | Purewal et al. | 424/45 |
| 5,254,330 | A | * | 10/1993 | Ganderton et al. | 424/46 |
| 5,260,306 | A | * | 11/1993 | Boardman et al. | 514/291 |
| 5,284,656 | A | | 2/1994 | Platz et al. | 424/435 |
| 5,288,498 | A | * | 2/1994 | Stanley et al. | 424/435 |
| 5,306,483 | A | | 4/1994 | Mautone | 424/45 |
| 5,320,094 | A | * | 6/1994 | Laube et al. | 424/440 |
| 5,341,800 | A | * | 8/1994 | Clark et al. | 128/203.12 |
| 5,348,730 | A | | 9/1994 | Greenleaf et al. | 424/45 |
| 5,349,947 | A | * | 9/1994 | Newhouse et al. | 424/45 |
| 5,352,461 | A | * | 10/1994 | Feldstein et al. | 424/493 |
| 5,354,562 | A | | 10/1994 | Platz et al. | 424/489 |
| 5,364,838 | A | | 11/1994 | Rudsamen | 514/3 |
| 5,376,359 | A | * | 12/1994 | Johnson | 514/3 |
| 5,376,386 | A | * | 12/1994 | Ganderton et al. | 424/46 |
| 5,384,133 | A | * | 1/1995 | Boyes et al. | 424/499 |

(List continued on next page.)

FOREIGN PATENT DOCUMENTS

| | | |
|---|---|---|
| AU | 43 556/93 | 1/1994 |
| DE | 1 208 036 | 11/1963 |
| DE | 26 20 446.6 | 5/1976 |

(List continued on next page.)

OTHER PUBLICATIONS

Budavari et al. (1989). The Merck Index. Merck & Co., Inc., pp. 1079 and 1107.*

Li et al., "Effect of a Conjugated Bile Salt on the Pulmonary Absorption of Insulin in Rats," Eur. J. Pharm. Biopharm, vol. 39, pp. 216–221, 1993.

Okumura et al., "Intratracheal delivery of insulin Absorption from solution and aerosol by rat lung," International Journal of Pharmaceutics, vol. 88, pp. 63–73, 1992.

(List continued on next page.)

*Primary Examiner*—José C. Dees
(74) *Attorney, Agent, or Firm*—Fish & Richardson P.C.

(57) ABSTRACT

A pharmaceutical aerosol formulation comprising (a) a HFA propellant; (b) a pharmaceutically active polypeptide dispersible in the propellant; and (c) a surfactant which is a $C_8$–$C_{16}$ fatty acid or salt thereof, a bile salt, a phospholipid, or an alkyl saccharide, which surfactant enhances the systemic absorption of the polypeptide in the lower respiratory tract. The invention also relates to methods of manufacturing such formulations and the use of such formulations in treating patients.

127 Claims, No Drawings

U.S. PATENT DOCUMENTS

| | | | | | |
|---|---|---|---|---|---|
| 5,419,315 | A | * | 5/1995 | Rubsamen | 424/501 |
| 5,437,271 | A | * | 8/1995 | Hodson et al. | 128/200.14 |
| 5,451,569 | A | * | 9/1995 | Wong et al. | 128/203.15 |
| 5,458,135 | A | * | 10/1995 | Patton et al. | 128/200.14 |
| 5,474,759 | A | | 12/1995 | Fassberg et al. | 424/45 |
| 5,482,032 | A | * | 1/1996 | Smith et al. | 514/3 |
| 5,482,706 | A | | 1/1996 | Igari et al. | 128/203.15 |
| 5,506,203 | A | | 4/1996 | Backstrom | 514/4 |
| 5,514,670 | A | | 5/1996 | Friedman et al. | 514/2 |
| 5,518,998 | A | | 5/1996 | Backstrom | 514/3 |
| 5,607,915 | A | | 3/1997 | Patton | |
| 5,653,962 | A | * | 8/1997 | Akehurst et al. | 424/45 |
| 5,658,878 | A | | 8/1997 | Bäckström et al. | 514/12 |
| 5,661,130 | A | | 8/1997 | Meezan et al. | 514/4 |
| 5,674,471 | A | * | 10/1997 | Akehurst et al. | 424/45 |
| 5,707,644 | A | | 1/1998 | Illum | 514/25 |
| 5,730,969 | A | | 3/1998 | Hora et al. | 424/434 |
| 5,744,123 | A | * | 4/1998 | Akehurst et al. | 424/45 |
| 5,747,445 | A | | 5/1998 | Bäckström et al. | 424/85 |
| 5,814,607 | A | | 9/1998 | Patton | 514/4 |
| 5,830,853 | A | | 11/1998 | Bäström et al. | 514/12 |
| 5,858,968 | A | | 1/1999 | Weiner et al. | 514/4 |
| 5,952,008 | A | * | 9/1999 | Backstrom | |
| 5,997,848 | A | | 12/1999 | Patton et al. | |
| 6,004,574 | A | * | 12/1999 | Backstrom | |
| 6,051,256 | A | | 4/2000 | Platz et al. | 424/434 |
| 6,165,976 | A | * | 12/2000 | Backstrom | |
| 6,306,440 | B1 | | 10/2001 | Bäckström et al. | |

FOREIGN PATENT DOCUMENTS

| | | | | |
|---|---|---|---|---|
| DE | 26 20 483 | | 12/1976 | |
| DE | 261 096 | A1 | 5/1983 | |
| EP | 0 023 359 | A2 | 7/1980 | A61K/9/06 |
| EP | 0 055 041 | | 12/1981 | |
| EP | 0 130 550 | | 6/1984 | |
| EP | 0 133 252 | | 7/1984 | |
| EP | 0 122 036 | | 10/1984 | |
| EP | 0 128 831 | | 12/1984 | A61K/45/06 |
| EP | 0 200 383 | | 4/1986 | |
| EP | 0 225 189 | | 11/1986 | |
| EP | 0 312 052 | A1 | 10/1987 | |
| EP | 0 272 097 | | 12/1987 | |
| EP | 0 364 235 | A1 | 4/1988 | |
| EP | 0 360 340 | | 9/1989 | |
| EP | 0 499 344 | A2 | 11/1989 | |
| EP | 0 360 340 | A1 | 3/1990 | |
| EP | 0 455 463 | | 11/1991 | |
| EP | 0 518 600 | A1 | 6/1992 | |
| EP | 518600 | * | 12/1992 | |
| EP | 0 518 600 | A1 | 12/1992 | |
| EP | 0 383 751 | | 9/1994 | |
| FR | 76 36431 | | 12/1976 | |
| GB | 837465 | | 6/1915 | |
| GB | 1 242 211 | | 8/1971 | |
| GB | 1 520 247 | | 8/1978 | |
| GB | 1 527 605 | | 10/1978 | |
| GB | 1 569 611 | | 6/1980 | |
| JP | 1 117 825 | | 5/1989 | |
| JP | 4 041 421 | | 2/1992 | |
| JP | 4 149 126 | | 5/1992 | |
| JP | 632 932 | | 1/1998 | |
| SE | 8007820-7 | | 11/1986 | |
| SE | 9400371-2 | | 2/1994 | |
| SE | 9302198-8 | | 5/1994 | |
| WO | WO 87/052213 | | 9/1987 | |
| WO | WO 88/09163 | | 12/1988 | |
| WO | WO 90/07333 | | 7/1990 | |
| WO | WO 91/04011 | | 4/1991 | |
| WO | WO 91/11495 | | 8/1991 | |
| WO | WO 91/14422 | | 10/1991 | |
| WO | WO 91/16038 | | 10/1991 | |
| WO | WO 91/16882 | | 11/1991 | |
| WO | WO 91/16929 | | 11/1991 | |
| WO | WO 91/18091 | | 11/1991 | |
| WO | WO 92/04069 | | 3/1992 | |
| WO | WO 92/06704 | | 4/1992 | |
| WO | WO 92/08446 | | 5/1992 | |
| WO | WO 93/25198 | | 12/1993 | |
| WO | WO94/07514 | | 4/1994 | |
| WO | WO 94/07514 | | 4/1994 | |
| WO | WO 94/22461 | | 10/1994 | |
| WO | WO 95/00128 | | 1/1995 | |
| WO | WO 95/00151 | | 1/1995 | |
| WO | WO 96/19206 | | 6/1996 | |
| WO | WO 96/19207 | | 6/1996 | |
| WO | WO 97/10850 | | 3/1997 | |

OTHER PUBLICATIONS

Yamamoto et al., "Absorption Enhancement of Intrapulmonary Administered Insulin by Various Absorption Enhancers and Protease Inhibitors in Rats," J. Pharm. Pharmacol, vol. 46, pp. 14–18, 1993.

Allenby et al., "The absorption of Insulin Across the Respiratory Tract of the Guinea–Pig" The Aerosol Society, Fourth Annual Conference, University of Surrey, Apr. 9–11, 1990.

Aungst et al., "Comparison of the effects of various transmucosal absorption promoters of buccal insulin delivery" Int. J. Pharm. (Netherlands) 53(3):227–235, 1989, (abstract).

Bjork, "Starch Microspheres as a Nasal Delivery System for Drugs" ACTA Universitatis Upsaliensis 103, 1993, Incomplete.

Bjork et al., "Degradable starch microspheres as a nasal delivery system for insulin" Int. J. Pharm 47:233–238, 1988.

Chandler et al., "Nasal absorption in rats. II Effect of enhancers on insulin absorption and nasal histology" Int. J. Pharm. 76:61–70, 1991.

Cutie et al., "The Role of Dispersing Agents in Inhalation and Intranasal Aerosol Suspensions" Aerosol Age, pp. 52–54, 1985.

Damasy et al., "Intranasal Insulin" Diabetes Res. and Clin Pract. 5:S163, 1988.

Edman et al., "Routes of Delivery: Case Studies:Nasal Delivery of Peptide Drugs" Advanced Drug Del. Rev. 8:165–177, 1992.

Gordon et al., "Nasal absorption of insulin: Enhancement by hydrophobic bile salts" Proc. Natl. Acad. Sci. 32:7419–7423, 1985.

Hirai et al., "Effect of Surfactants on the Nasal Absorption of Insulin in Rats" Int. J. Pharm. 9:165–172, 1981.

Igawa et al., "Effect of Absorption Promoters in Intranasal Administration of Human Fibroblast Interferon . . . " Chem. Pharm. Bull. 37:418–421, 1989.

Komada et al., "Intratracheal Delivery of Peptide and Protein Agents: Absorption from Solution and Dry Powder by Rat Lung" J. Pharm. Sciences 83:863, 1994.

Lee et al., "Mucosal Penetration Enhancers for Facilitation of Peptide and Protein Drug Absorption" Crit. Rev. Therapeutic Drug Carrier Systems 8(2):91–192, 1991.

Lee et al., "Intranasal Bioavailability of Insulin Powder Formulations . . . " J. Pharm. Sciences 80(8):725, 1991, Incomplete title.

Mishima et al., "Studies on the Promoting Effects of Medium Chain Fatty Acid Salts on the Nasal Absorption . . . " J. Pharm. Dyn. 10:624–631, 1987.

Morita et al., "Effects of Various Absorption Promoters on Pulmonary Absorption of Drugs . . . " Biol. Pharm. Bull. 16:269–262, 1993, Incomplete title.

Moses et al., "Insulin Administered Intranasally as an Insulin–Bile Salt Aerosol" Diabetes 32:1040, 1983.

Olanoff et al., "Method to Enhance Intranasal Peptide Delivery" American Chemical Society Symposium, Lee & Good, eds., New York, Apr. 13–18, 1986.

Pontiroli et al., "Nasal administration of glucagon and human calcitonin to healthy subjects: a comparison of powders . . . " Eur. J. Clin. Pharmacol. 37:427–430, 1989.

SanGiovanni, "Just how practical is aerosolized nasal insulin" Spray Tech. & Marketing 2(1):16–19, 1992.

Schipper et al., "Nasal Insulin Delivery with Dimethyl–B–Cyclodextrin as an Absorption Enhancer in Rabbits . . . " Pharm. Res. 10:682, 1993.

Touitou et al., "Targeted Enteral Delivery of Insulin to Rats" Int. J. Pharm. (AMST) 30:95–100, 1986.

Wearley, "Recent Progress in Protein and Peptide Delivery by Noninvasive Routes" Crit. Rev. in Therapeutic Drug Carrier Systems 8(4):331–394, 1991.

Wigley et al., "Insulin Across Respiratory Mucosae by Aerosol Delivery" Diabetes 20(8):552, 1971.

Yoshida et al., "Absorption of Insulin Delivered to Rabbit Trachea Using Aerosol Dosage Form" J. of Pharm. Sciences 68:670, 1979.

Zinman, "The physiologic replacement of insulin" Medical Intelligence: Drug Therapy 321:363, 1989.

Almer et al. "Insulin Inhalation—At Last A Breakthrough," *Diabetes Res. And Clin. Pract.,* 5:s163 (1988).

Aungst and Rogers, "Comparison of the Effects of Various Transmucosal Absorption Promoters on Buccal Insulin Delivery," *Int. J. Pharm.* (Netherlands), 53/3, 227–235 (1989).

Björk et al., "Characterization of degradable starch . . . " *International Journal of Pharmaceutics,* 62 (1990) 187–192.

Brange et al., "Monomeric Insulins and Their Experimental and Clinical Implications," *Diabetes Care,* 13:923–954 (1990).

Byron et al., "Drug Delivery via the Respiratory . . . ," *Journal of Aerosol Medicine,* 7:49–75 (1994).

Chien et al., "Intranasal Drug Delivery for Systemic Medications," *CRC Critical Reviews in Therapeutic Drug Carrier Systems,* 4:67–194 (1987).

Chien et al., "Potential Developments in Systemic Delivery of Insulin," *Drug Development and Industrial Pharmacy,* 15(10), 1601–1634 (1989).

Colthorpe et al., "The Pharmacokinetics of Pulmonary–Delivered Insulin: A Comparison of Intratracheal . . . ," *Pharmaceutical Research,* vol. 9, No. 6, pp. 764–769 (1992).

Dahlbäck et al., "Deposition of Tracer Aerosols in the Rabbit Respiratory Tract," *Journal of Aerosol Science,* vol. 18, No. 6, pp. 733–736 (1987).

Dahlbäck et al., "Regional Administration of Drugs to the Rabbit Respiratory Tract. Effects on Absorption," *Journal of Aerosol Medicine,* 1:222–223 (1988).

Dempster et al., Anabolic Actions of Parathyroid Hormone on Bone, *Endocrine Reviews* 14:690–709, (1993).

"Diabetes Mellitus", Ch. VI in *Scientific American Medicine,* Scientific American, Inc., Apr. 1993.

The Diabetes Control and Complications Trial Research Group, "The Effect of Intensive Treatment of Diabetes on the Development . . . Complications in Insulin–Dependent Diabetes Mellitus," *New England Journal of Medicine,* 329:977–986 (1993).

Elliot et al., "Parenteral absorption of insulin . . . ," *Austr. Paediatr. J.,* 23:293–297 (1987).

Eppstein and Longenecker, "Alternative Delivery Systems for Peptides and Proteins as Drugs," *CRC Critical Reviews in Therapeutic Drug Carrier Systems,* 5:99–139 (1988).

Goni et al., "Palmitoylcarnitine, a surface–active metabolite," *FEBS Lett.,* vol. 390, pp. 1–5 (1996).

Hoover et al., "Peptides are Better Absorbed from the Lung than the Gut in the Rat," *Pharmaceutical Research,* vol. 9, No. 8, pp. 1103–1106 (1992).

Jacobs, Maarten A.J.M., "The Pharmacodynamics and Activity of Intranasally Administered Insulin in Healthy Male Volunteers," *Diabetes,* vol. 42, pp. 1649–1655 (1993).

Jaegfeldt, H. et al., "Particle size distribution from different modifications of Turbuhaler®," Proceedings of an international workshop on a new inhaler, May 21–22, 1987 (London) pp. 90–99.

Jones, "Pulmonary absorption of insulin", (1998) Ph.D. Thesis, Welsh School of Pharmacy, University of Wales, United Kingdom.

Köhler, Dieter, "Aerosols for Systemic Treatment," *Lung,* Supplement: 677–684 (1990).

Köhler et al., "Nicht radioaktives Verfahren zur Messung der Lungenpermeabilitat: Inhalation von Insulin," *Aten–w–Lungenkrkh,* Jahrgang 13, Nr. Jun. 1987; 230–232.

Lasker, "The Diabetes Control and Complications Trial," *The New England Journal of Medicine,* 329:1035–1036 (1993).

Laube et al., "Preliminary Study of the Efficacy of Insulin Aerosol Delivery by Oral Inhalation in Diabetic Patients," *Journal of the American Medical Association,* 239:2106–2109 (1993).

Lecluyse et al., "In Vitro Effects of Long–Chain Acylcarnitines on the Permeability, Transepithelial Electrical Resistance and Morphology of Rat Colonic Mucosa," *J. Pharmacol. Exp. Ther.,* vol. 265(2), pp. 955–962 (1993).

Lee et al., "Development of an aerosol dosage form containing insulin," *Journal of Pharmaceutical Sciences,* vol. 65, No. 4, pp. 567–574 (1976).

Liu et al., "Pulmonary Delivery of Free . . . ," *Pharmaceutical Research,* 10:228–232 (1993).

Longenecker et al., "Effects of Sodium Taurodihydrofusidate on Nasal Absorption of Insulin in Sheep," *J. Pharm. Sci.,* 76(5):351–355 (1987).

Nagai et al., "Powder Dosage Form of Insulin for Nasal Administration," *J. Controlled Release,* 1:15–22 (1984).

Nagano et al., "New Method of Insulin . . . ," *Jikeikai Medical Journal,* 32: 503–506 (1985).

Newman, "Chapter 9: Therapeutic aerosols", In: *Aerosols and the Lung: Clinical and Experimental Aspects,* (1984) Butterworth & Co., United Kingdom.

O'Hagan and Illum, "Absorption of Peptides and Proteins from the Respiratory Tract and the Potential for Development of Locally Administered Vaccine," *Critical Reviews in Therapeutic Drug Carrier Sys,* 7:35–97 (1990).

Patton et al., "Bioavailability of Pulmonary Delivered Peptides and Proteins: α–interferon, Calcitonins and Parathyroid Hormones," *Journal of Controlled Release,* 28: 79–85 (1994).

Patton et al., "(D) Routes of Delivery: Case Studies," *Advanced Drug Delivery Reviews,* vol. 8, pp. 179–196 (1992).

Reeve et al., Anabolic Effect of Human Parathyroid Hormone Fragment on Trabecular Bone in Involutional Osteoporosis: A Multicentre Trial, British Medical Journal, pp. 1340–1344, (1980).

*Remington's Pharmaceutical Science,* $18^{th}$ edition, p. 1079 (1990).

Ruin, "Diabetics May Not Need Their Insulin Shots," article in Sydsvenska (Dagladet), Monday, Jun. 12, 1989.

Sakr, "A New Approach for insulin . . . ," *International Journal of Pharmaceutics,* 86:1–7 (1992).

Salzman et al., "Intranasal Aerosolized Insulin Mixed–Meal Studies and Long–term Use in Type 1 Diabetes," *The New England Journal of Medicine,* 1312:1078–1084 (1985).

Schanker et al., "Species Comparison of Drug Absorption from the Lung Aerosol Inhalation or Intratracheal Injection," *Drug Metabolism & Disposition,* vol. 14, pp. 79–88 (1986).

Schluter et al., "Pulmonary Administration . . . Type 1 Diabetics" Abstract #298, *Diabetes,* 33 (Supplement): 75A (1984).

Selam and Charles, "Devices for Insulin Administration," *Diabetes Care,* 13:955–979 (1990).

Timsina et al., "Drug Delivery to the Respiratory Tract Using Dry Powder Inhalers," *Int. J. Pharmaceutics,* 101:1–13 (1994).

Wang et al., *Parental Science and Technology,* 42 (2S), S4–S26, 1988.

Wetterlin, Kiell, "Turbuhaler: A New Powder Inhaler for Administration of Drugs to the Airways," *Pharmaceutical Research,* vol. 5, pp. 506–508, (1988).

Zingg et al., "Transhepatic Absorption and Biliary Excretion of Insulin," *Can. J. Physiol. Pharmacol.,* 65:1982–1987 (1987).

* cited by examiner

AEROSOL FORMULATIONS OF PEPTIDES AND PROTEINS

This application is a 371 of PCT/SE95/01540 filed Dec. 19, 1995.

This invention relates to drug formulations containing medically useful peptides and proteins, for inhalation from an aerosol inhaler.

BACKGROUND OF THE INVENTION

A range of drugs are administered in aerosol formulations through the mouth or nose. One widely used method for dispensing such an aerosol formulation involves making a suspension formulation of the drug as a finely divided powder in a liquefied gas known as a propellant. Pressurised metered dose inhalers, or pMDI's, are normally used to dispense such formulations to a patient. Surface active agents, or surfactants, are commonly included in order to aid dispersion of the drug in the propellant and to prevent aggregation of the micronised drug particles.

Until recently, chlorofluorocarbon-containing propellants (CFC's) were accepted for use in all pharmaceutical aerosol formulations. Typical surfactant dispersing agents used in the CFC formulations were for example sorbitantrioleate, oleic acid, lecithines, and ethanol. Since CFC's have been implicated in the destruction of the ozone layer, a new generation of propellants has emerged to take their place.

Hydrofluoroalkane (HFA) propellants such as 1,1,1,2-tetrafluoroethane (P134a), 1,1,1,2,3,3,3-heptafluoropropane (P227) and 1,1-difluoroethane (P152a) are considered to be the most promising new propellants. Not only are they environmentally acceptable, but they also have low toxicity and vapour pressures suitable for use in aerosols. However the surfactants normally used in CFC-aerosol formulations are not particularly suitable for use with the new generation of propellants and therefore in recent years a number of alternative surfactants have been suggested for use specifically with the HFA propellants, among them polyethoxylated surfactants and fluorinated surfactants.

Peptide-based drugs have not traditionally been among those drugs which are administered from aerosol formulations, although various aerosol formulations have been suggested.

For example U.S. Pat. No. 5,284,656 discloses a formulation of granulocyte colony stimulating factor (G-SCF) comprising a finely divided powder containing G-SCF suspended in a propellant, with the aid of a surfactant such as sorbitan trioleate, soya lecithin or oleic acid. U.S. Pat. No. 5,364,838 discloses an insulin formulation wherein a dry powder of insulin is suspended within a low boiling point propellant with an excipient such as oleic acid.

SUMMARY OF THE INVENTION

We have now surprisingly found that various substances which enhance the absorption of polypeptides in the respiratory tract are also particularly suitable as surfactants for use with HFA propellants.

The invention thus provides a pharmaceutical aerosol formulation comprising (a) a HFA propellant; (b) a pharmaceutically active polypeptide dispersible in the propellant; and (c) a surfactant which is a $C_8$–$C_{16}$ fatty acid or salt thereof, a bile salt, a phospholipid, or an alkyl saccharide, which surfactant enhances the systemic absorption of the polypeptide in the lower respiratory tract.

The surfactants employed in the present invention are surprisingly suitable for use with HFA propellants; their capabilities for enhancement of the absorption of polypeptide give them a dual function which makes them especially beneficial for use in the present polypeptide aerosol formulations.

Of the fatty acids and salts thereof, $C_8$–$C_{16}$ fatty acids salts are preferred. Examples of preferred fatty acid salts are sodium, potassium and lysine salts of caprylate ($C_8$), caprate ($C_{10}$), laurate ($C_{12}$) and myristate ($C_{14}$). As the nature of the counterion is not of special significance, any of the salts of the fatty acids are potentially useful. A particularly preferred fatty acid salt is sodium caprate.

Suitable bile salts may be for example salts of cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid.

Of the bile salts, trihydroxy bile salts are preferred. More preferred are the salts of cholic, glycocholic and taurocholic acids, especially the sodium and potassium salts thereof. The most preferred bile salt is sodium taurocholate.

Suitable phospholipids may be for example single-chain phospholipids, for example lysophosphatidylcholine, lysophosphatidylglycerol, lysophosphatidylethanolamine, lysophosphatidylinositol and lysophosphatidylserine or double-chain phospholipids, for example diacylphosphatidylcholines, diacylphosphatidylglycerols, diacylphosphatidylethanolamines, diacylphosphatidylinositols and diacylphosphatidylserines.

Of the phospholipids, diacylphosphatidylglycerols and diacylphosphatidylcholines are preferred, for example dioctanoylphosphatidylglycerol and dioctanoylphosphatidylcholine.

Suitable alkyl saccharides may be for example alkyl glucosides or alkyl maltosides, such as decyl glucoside and dodecyl maltoside.

The most preferred surfactants are bile salts.

The propellant may comprise one or more of 1,1,1,2-tetrafluoroethane (P134a), 1,1,1,2,3,3,3-heptafluoropropane (P227) and 1,1-difluoroethane (P152a), for example, optionally in admixture with one or more other propellants. Preferably the propellant comprises P134a or P227, or a mixture of P134a and P227, for example a density-matched mixture of p134a and P227.

The polypeptide may be any medically or diagnostically useful peptide or protein of small to medium size, i.e. up to about 40 kD molecular weight (MW), for which systemic delivery is desired. The mechanisms of improved polypeptide absorption according to the present invention are generally applicable and should apply to all such polypeptides, although the degree to which their absorption is improved may vary according to the MW and the physico-chemical properties of the polypeptide, and the particular surfactant used. It is expected that polypeptides having a molecular weight of up to 30 kD will be most useful in the present invention, such as polypeptides having a molecular weight of up to 25 kD or up to 20 kD, and especially up to 15 kD or up to 10 kD.

The polypeptide is preferably a peptide hormone such as insulin, glucagon, C-peptide of insulin, vasopressin, desmopressin, corticotropin (ACTH), corticotropin releasing hormone (CRH), gonadotropin releasing hormone (GnRH), gonadotropin releasing hormone agonists and antagonists, gonadotrophin (luteinizing hormone, or LHRH), is calcitonin, parathyroid hormone (PTH), bioactive fragments of PTH such as PTH(34) and PTH(38), growth hormone (GH) (for example human growth hormone (hGH)), growth hormone releasing hormone (GHRH), somatostatin, oxytocin, atrial natriuretic factor (ANF), thyrotropin releasing hormone (TRH), prolactin, and follicle stimulating hormone (FSH), and analogues of any of the above.

Other possible polypeptides include growth factors, interleukins, polypeptide vaccines, enzymes such as deoxyribonuclease (DNase), endorphins, glycoproteins, lipoproteins, and polypeptides involved in the blood coagulation cascade, that exert their pharmacological effect systemically. It is expected that most if not all polypeptides of small to medium size can be effectively delivered by the methods of the invention.

The preferred polypeptide is insulin.

In addition to drug, propellant and surfactant, a small amount of ethanol (normally up to 5% but possibly up to 20%, by weight) may be included in the formulations of the present invention. Ethanol is commonly included in aerosol compositions as it can improve the function of the metering valve and in some cases also improve the stability of the dispersion.

The composition may of course contain other additives as needed, including other pharmaceutically active agents, adjuvents, carriers, flavouring agents, buffers, antioxidants, chemical stabilisers and the like. As examples of suitable additives may be mentioned for exanple lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

The preferred carrier is melezitose.

The formulation of the present invention is particularly advantageous because of the dual function of the particular surfactants employed. The surfactants as provided in the present invention are not only surprisingly capable of producing fine dispersions in the new generation of propellants, but, very importantly, also enhance polypeptide absorption. The present formulations are stable and bioavailability of the polypeptides is high, with good reproducibility.

The surfactants used in the present invention may enhance the absorption of the polypeptide by for example (1) Enhancement of the paracellular permeability of a polypeptide by inducing structural changes in the tight junctions between the epithelial cells.

(2) Enhancement of the transcellular permeability of a polypeptide by interacting with or extracting protein or lipid constituents of the membrane.

(3) Interaction between enhancer and polypeptide which increases the solubility of the polypeptide in aqueous solution. This may occur by preventing formation of polypeptide aggregates (dimers, trimers, hexamers), or by solubilizing polypeptide molecules in enhancer micelles.

(4) Decreasing the viscosity of, or dissolving, the mucus barrier lining the alveoli and passages of the lung, thereby exposing the epithelial surface for direct absorption of the polypeptide.

(5) Reducing the activity of protease inhibitors in the lungs, thereby increasing the stability of the polypeptide, increasing absorption.

The surfactants may function by only a single mechanism set forth above, or by two or more. A surfactant acting by several mechanisms is more likely to promote efficient absorption of a polypeptide than one which employs only one or two.

By "enhances absorption" is meant that the amount of polypeptide absorbed into the systemic circulation in the presence of surfactant is higher than in its absence.

Preferably the surfactant is present in the present invention in a surfactant: polypeptide ratio in the range of approximately 1:10 to 1:0.2, preferably 1:4 to 1:1, more preferably 1:4 to 1:2.5. The preferred concentration of polypeptide in the formulations of the present invention is 0.1 mg/ml to 25 mg/ml.

As much as possible of the polypeptide preferably consists of particles having a diameter of less than 10 microns, for example 0.01–10 microns or 0.1–6 microns, for example 0.1–5 microns. Preferably at least 50% of the polypeptide consists of particles within the desired size range. For example at least 60%, preferably at least 70%, more preferably at least 80% and most preferably at least 90% of the polypeptide consists of particles within the desired size range.

Therefore, the polypeptide for use in the present invention may have to be processed prior to inclusion in the formulations, in order to produce particles in the desired size range. For example the polypeptide may be micronised, for example in a suitable mill, such as a jet mill. Alternatively, particles in the desired particle range may be obtained by for example spray drying or controlled crystallisation methods, for example crystallisation using supercritical fluids.

Preferably, the surfactant for use in the present invention also consists of particles within the desired size range. Suitably, the polypeptide and surfactant may be mixed in an aqueous buffer and dried to give a solid powder which is then optionally micronised. The micronised powder may then be added to a fraction of the propellant (and optional ethanol) at low temperature. After mixing in of the drug the remaining surfactant and propellant and optionally ethanol may be added and the suspension filled into appropriate containers.

The polypeptide aerosol formulation of the present invention is useful for the local or systemic treatment of diseases and may be administered for example via the upper and lower respiratory tract, including by the nasal route. As such the present invention also is provides said polypeptide aerosol formulation for use in therapy; the use of the polypeptide aerosol formulation in the manufacture of a medicament for the treatment of diseases via the respiratory tract; and a method for the treatment of a patient in need of therapy, comprising administering to said patient a therapeutically effective amount of the polypeptide aerosol formulation of the present invention.

The diseases which may be treated with the polypeptide aerosol formulation of the present invention are any of those which may be treated with the particular polypeptide in each case; for example formulations containing insulin according to the present invention may be used for example in the treatment of diabetes; formulations containing corticotropin may be used for example in the treatment of inflammatory diseases; formulations containing GnRH may be useful for example in the treatment of male infertility. The indications for all of the mentioned polypeptides are well known. The polypeptide aerosol formulations of the present invention may also be used in prophylatic treatment.

The following Examples are intended to illustrate, but not limit, the invention:

Formulations of insulin in P134a and/or P227 with different surfactants were prepared in order to assess the quality of the suspensions formed. In the following examples the quality of the suspension is rated as "acceptable" or "good". An acceptable suspension is characterised by one or more of slow settling or separation, ready re-dispersion, little flocculation, and absence of crystallisation or morphology changes, such that the dispersion is sufficiently stable to give a uniform dosing. A good dispersion is even more stable.

EXAMPLE 1

Method

Insulin (65–25 parts, as below) was added to a beaker with water and dissolved. Surfactant (25–35 parts, as below) was added and dissolved and the pH was adjusted to 7.4 The solution was concentrated by evaporation of the water. The obtained solid cake was crushed, sieved and micronised in a jet mill. 40 or 50 mg of the powder was added to a plastic coated glass bottle. The bottle was chilled to approximately −40° C. with a mixture of carbon dioxide ice and isopropanol, and 10 ml chilled P134a (at approximately −40° C.) was added. The bottle was sealed with a metering valve and then shaken vigorously for about 30 seconds. Examples 1g to 1n were additionally treated in an ultrasonic bath for about 10 minutes.

Results

| Example No. | Surfactant | Ratio sulfactant:insulin | Suspension |
|---|---|---|---|
| 1a | sodium caprate | 25:75 | good |
| 1b | potassium caprate | 27:73 | good |
| 1c | lysine caprate | 35:65 | good |
| 1d | sodium myristate | 30:70 | good |
| 1e | sodium laurate | 25:75 | good |
| 1f | sodium caprylate | 25:75 | good |
| 1g | sodium taurocholate | 25:75 | good |
| 1h | dioctanoylphosphatitidyl glycerol | 25:75 | good |
| 1j | dodecylmaltoside | 25:75 | good |
| 1k | lysopalmitoylphosphatidyl glycerol | 25:75 | acceptable |
| 1m | lysopalmitoylphosphatidyl choline | 25:75 | acceptable |
| 1n | dioctanoylphosphatidyl choline | 25:75 | good |

EXAMPLE 2

Sodium caprate (25 parts) and insulin (75 parts) were micronised separately and then dry mixed. 40 mg of this mixture was added to a plastic coated glass bottle. The bottle was chilled to approximately −40° C. with a mixture of carbon dioxide ice and isopropanol, and 10 ml chilled (approximately −40° C. P134a was added. The bottle was sealed with a metering valve and then shaken vigorously for about 30 seconds. A good suspension formed.

EXAMPLE 3

Method

Insulin (65–75 parts, as below) was added to a beaker with water and dissolved. Surfactant (25–35 parts, as below) was added and dissolved and the pH was adjusted to 7.4. The solution was concentrated by evaporation of the water. The obtained solid cake was crushed, sieved and micronised in a jet mill. 40 or 50 mg of the powder was added to a plastic coated glass bottle. The bottle was chilled to approximately −40° C. with a mixture of carbon dioxide ice and isopropanol, and 10 ml chilled (approximately −40° C.) P227 was added. The bottle was sealed with a metering valve and then shaken vigorously for about 30 seconds. Examples 3g to 3n were additionally treated in an ultrasonic bath for about 10 minutes.

Results

| Example No. | Surfactant | Ratio surfactant:insulin | Suspension |
|---|---|---|---|
| 3a | sodium caprate | 25:75 | good |
| 3b | potassium caprate | 27:73 | good |
| 3c | lysine caprate | 35:65 | good |
| 3d | sodium myristate | 30:70 | good |
| 3e | sodium laurate | 25:75 | good |
| 3f | sodium caprylate | 25:75 | good |
| 3g | sodium taurocholate | 25:75 | good |
| 3h | dioctanoylphosphatitidyl glycerol | 25:75 | good |
| 3j | dodecylmaltoside | 25:75 | good |
| 3k | lysopalmitoylphosphatidyl glycerol | 25:75 | acceptable |
| 3m | lysopalmitoylphosphatidyl choline | 25:75 | acceptable |
| 3n | dioctanoylphosphatidyl choline | 25:75 | good |

EXAMPLE 4

Micronised formulations containing DNase, surfactant (sodium taurocholate or dioctanoylphosphatidylglcerol), and melezitose (ratio DNase: surfactant: melezitose 1: 0.33:98.67, total weight 50 mg), were added to a plastic coated glass bottle, chilled to approximately −40° C. Chilled propellant 134a or propellant 227 (approximately −40° C., approximately 10 ml) was added and the bottles sealed with a metering valve and treated in an ultrasonic bath for approximately 10 minutes.

Identical formulations were prepared to which 5% (w/w) of ethanol was added prior to the treatment in the ultrasonic bath.

The quality of the suspensions formed were assessed immediately and after storage at room temperature for 20 hours. In all cases good suspensions were observed.

EXAMPLE 5

Sodium caprate and insulin were micronised separately and then dry mixed. The proportion of sodium caprate to insulin was 25:75. 80 mg of this mixture was added to an aerosol vial. The aerosol vial was chilled to approximately --40° C. with a mixture of carbon dioxide ice and isopropanol, and 10 ml chilled (approximately −40° C. ) P134a was added. The aerosol vial was sealed with a 50 $\mu$l metering valve and then treated for a couple of minutes in an ultra sonic bath.

The particle size of insulin in the aerosol delivered from the container was measured with an "Andersen" impactor at 28.3 lit/min. The fraction of fine particles (less than 6 $\mu$m) was 41% of the delivered dose. The particle measurement was repeated after storage for two months at room temperature and no deterioration was observed. The fine particle fraction was 46%.

EXAMPLE 6

50 aerosol units containing insulin and sodium taurocholate (ratio 75:25, 8 mg/ml) were prepared as follows: The substances were weighed into a beaker. The beaker was chilled to approximately −40° C. with a mixture of carbon dioxide and isopropanol. Propellant (p134a, approximately −40° C.) was added, the mixture was mixed for a few minutes with an ultraturrax, then poured into a manufacturing vessel, and further propellant (p134a, approximately −40° C.) was added. (Total volume 500 ml) The formulation was stirred with an ultraturrax and filled into metered dose inhalers, 10 ml in each. The inhalers were sealed with metering valves.

The aerosols were stored in varying conditions:

| | |
|---|---|
| 5° C., dry conditions | for 2, 8, and 13 weeks |
| 30° C., 30% relative humidity | for 11 weeks |

The quality of the suspensions assessed. In all cases good suspensions was were observed.

In addition the stability of the insulin was assessed by measuring, using standard chromatographical techniques, the concentration of the degradation products desamido insulin and other insulin-related impurities. In all cases the level of impurities was within acceptable limits (less than 5% desamido insulin and less than 3% other insulin-related impurities).

EXAMPLE 7

A pressurised metered dose inhaler filled with the preparation of Example 5 was actuated, and the delivered aerosol collected in a spacer. An airflow (8 lit/min) was led through the spacer into the delivery system, to which each of five dogs were exposed for five minutes. The target inhaled dose was 1U.insulin/kg. The bioavailability was determined by comparison of the plasma curve after inhalation and the plasma curve after intravenous injection from earlier studies. The bioavailability was 66% of the drug reaching the lungs.

EXAMPLE 8

Pressurised metered dose inhalers were filled with the formulation of Example 6 or with a corresponding formulation without enhancer. Each inhaler was actuated, and the delivered aerosol collected in a spacer. An airflow (8 lit/min) was led through the spacer into the delivery system, to which each of five dogs were exposed for two minutes. The target inhaled dose was 1U.insulin/kg. Blood samples were collected before dosing and at various time intervals up to 245 minutes after the start of dosing. The plasma insulin concentration was measured by radioimmunoassay.

From the formulations without enhancer, the insulin was in general absorbed relatively slowly, with peak plasma insulin levels occuring between 50 and 100 minutes after administration is some of the animals. In other animals peak plasma insulin levels occured between 10 and 20 minutes after administration.

From the formulations according to the invention, a peak plasma insulin level was reached in all animals within 10 minutes of adminstration, followed by another peak at around 25 minutes, in all animals.

The generally faster absorption of insulin from the formulations according to the invention is closer to the natural insulin plasma curve following meals, in healthy people. Moreover the lack of variation between animals indicates that a desired level of insulin absorption is easier and more reliably achieved using the formulations of the present invention.

What is claimed is:

1. A pharmaceutical aerosol formulation comprising (a) a HFA propellant; (b) a pharmaceutically active polypeptide dispersible in the propellant; and (c) a surfactant which is a $C_8$–$C_{16}$ fatty acid salt, a bile salt, a single-chain phospholipid, or an alkyl saccharide, which surfactant enhances the systemic absorption of the polypeptide in the lower respiratory tract.

2. A pharmaceutical aerosol formulation as claimed in claim 1, wherein the surfactant is a $C_8$–$C_{16}$ fatty acid salt.

3. A pharmaceutical aerosol formulation as claimed in claim 2, wherein the fatty acid salt is selected from the sodium, potassium and lysine salts of caprylate ($C_8$), caprate ($C_{10}$), laurate ($C_{12}$) and myristate ($C_{14}$).

4. A pharmaceutical aerosol formulation as claimed in claim 1, wherein the surfactant is a trihydroxy bile salt.

5. A pharmaceutical aerosol formulation as claimed in claim 4, wherein the bile salt is selected from the salts of cholic, glycocholic and taurocholic acids.

6. A pharmaceutical aerosol formulation as claimed in claim 5, wherein the bile salt is selected from the sodium and potassium salts of cholic, glycocholic and taurocholic acids.

7. A pharmaceutical aerosol formulation as claimed in claim 6, wherein the bile salt is sodium taurocholate.

8. A pharmaceutical aerosol formulation as claimed in claim 1, wherein the surfactant is a single-chain phospholipid.

9. A pharmaceutical aerosol formulation as claimed in claim 8, wherein the surfactant is selected from lysophosphatidylcholines, lysophosphatidylglycerols, lysophosphatidylethanolamines, lysophosphatidylinositols and lysophosphatidylserines.

10. A pharmaceutical aerosol formulation as claimed in claim 1, wherein the sufactant is selected from alkyl glucosides and alkyl maltosides.

11. A pharmaceutical aerosol formulation as claimed in claim 10, wherein the surfactant is selected from decyl glucoside and dodecyl maltoside.

12. A pharmaceutical aerosol formulation as claimed in claim 1, wherein the propellant comprises 1,1,1,2-tetrafluoroethane (P134a); 1,1,1,2,3,3,3-heptafluoropropane (P227) or 1,1-difluoroethane (P152a).

13. A pharmaceutical aerosol formulation as claimed in claim 12, wherein the propellant comprises 1,1,1,2-tetrafluoroethane (P134a) and 1,1,1,2,3,3,3-heptafluoropropane (P227).

14. A pharmaceutical aerosol formulation as claimed in claim 13, wherein the propellant comprises a density-matched mixture of 1,1,1,2-tetrafluoroethane (P134a) and 1,1,1,2,3,3,3-heptafluoropropane (P227).

15. A pharmaceutical aerosol formulation as claimed in claim 1, wherein the polypeptide is of molecular weight up to 40 kD.

16. A pharmaceutical aerosol formulation as claimed in claim 15, wherein the polypeptide is of molecular weight up to 30 kD.

17. A pharmaceutical aerosol formulation as claimed in claim 16, wherein the polypeptide is of molecular weight up to 25 kD.

18. A pharmaceutical aerosol formulation as claimed in claim 17, wherein the polypeptide is of molecular weight up to 15 kD.

19. A pharmaceutical aerosol formulation as claimed in claim 18, wherein the polypeptide is of molecular weight up to 10 kD.

20. A pharmaceutical aerosol formulation as claimed in claim 1, wherein the polypeptide is a peptide hormone.

21. A pharmaceutical aerosol formulation as claimed in claim 1, wherein the polypeptide is selected from the group consisting of insulin, glucagon, C-peptide of insulin, vasopressin, desmopressin, corticotropin (ACTH), corticotropin releasing hormone (CRH), gonadotropin releasing hormone (GnRH), gonadotropin releasing hormone agonists and antagonists, gonadotropin, calcitonin, parathyroid hormone (PTH), bioactive fragments of PTH, growth hormone (GH), growth hormone releasing hormone (GHRH), somatostatin, oxytocin, atrial natriuretic factor (ANF), thyrotropin releasing hormone (TRH), deoxyribonuclease (DNase), prolactin, and follicle stimulating hormone (FSH), and biologically active analogues thereof.

22. A pharmaceutical aerosol formulation as claimed in claim 21, wherein the polypeptide is insulin.

23. A pharmaceutical aerosol formulation as claimed in claim 1, including ethanol in an amount of up to 20% by weight of propellant and surfactant.

24. A pharmaceutical aerosol formulation as claimed in claim 1, including ethanol in an amount of up to 5% by weight of propellant and surfactant.

25. A pharmaceutical aerosol formulation as claimed in claim 1, additionally comprising an additive selected from the group consisting of adjuvants, carriers, flavouring agents, buffers, antioxidants and chemical stabilisers.

26. A pharmaceutical aerosol formulation as claimed in claim 25, wherein the additive is selected from the group consisting of lactose, glucose, fructose, galactose, trehalose, sucrose, maltose, raffinose, maltitol, melezitose, stachyose, lactitol, palatinite, starch, xylitol, mannitol, myoinositol, a hydrate of any of the aforementioned carbohydrates, alanine, glycine, betaine, and albumen.

27. A pharmaceutical aerosol formulation as claimed in claim 26, wherein the additive is melezitose.

28. A pharmaceutical aerosol formulation as claimed in claim 1, wherein the surfactant is present in a surfactant:polypeptide ratio in the range of 1:10 to 1:0.2.

29. A pharmaceutical aerosol formulation as claimed in claim 28, wherein the surfactant is present in a surfactant:polypeptide ratio in the range of 1:4 to 1:1.

30. A pharmaceutical aerosol formulation as claimed in claim 1, wherein at least 50% of the polypeptide consists of particles having a diameter of 0.01–10 microns.

31. A pharmaceutical aerosol formulation as claimed in claim 30, wherein at least 50% of the polypeptide consists of particles having a diameter of 0.1–6 microns.

32. A pharmaceutical aerosol formulation as claimed in claim 30, wherein at least 50% of the polypeptide consists of particles having a diameter of 0.1–5 microns.

33. A pharmaceutical aerosol formulation as claimed in claim 30, wherein at least 70% of the polypeptide consists of particles having a diameter of 0.01–10 microns.

34. A pharmaceutical aerosol formulation as claimed in claim 31, wherein at least 70% of the polypeptide consists of particles having a diameter of 0.1–6 microns.

35. A pharmaceutical aerosol formulation as claimed in claim 32, wherein at least 70% of the polypeptide consists of particles having a diameter of 0.1–5 microns.

36. A pharmaceutical aerosol formulation as claimed in claim 30, wherein at least 90% of the polypeptide consists of particles having a diameter of 0.01–10 microns.

37. A pharmaceutical aerosol formulation as claimed in claim 32, wherein at least 90% of the polypeptide consists of particles having a diameter of 0.1–5 microns.

38. A pharmaceutical aerosol formulation as claimed in claim 1, wherein the concentration of polypeptide is 0.1 mg/ml to 25 mg/ml of the formulation.

39. A method for the manufacture of a pharmaceutical aerosol formulation as claimed in claim 1, comprising the steps of: mixing the polypeptide and the surfactant in an aqueous buffer; drying to give a solid powder; and mixing the powder and the propellant in a vessel.

40. A method as claimed in claim 39, wherein said mixing step is carried out by first mixing a portion of the propellant with the powder in the vessel, and then adding the remaining propellant to the vessel.

41. A method for the treatment of a patient in need of therapy with a given polypeptide, comprising administering to said patient a therapeutically effective amount of the pharmaceutical aerosol formulation of claim 1, provided that the pharmaceutically active polypeptide in the formulation is said given polypeptide.

42. A method as claimed in claim 41, wherein the surfactant is a $C_8$–$C_{16}$ fatty acid salt.

43. A method as claimed in claim 41, wherein the fatty acid salt is selected from the sodium, potassium and lysine salts of caprylate ($C_8$), caprate ($C_{10}$), laurate ($C_{12}$) and myristate ($C_{14}$).

44. A method as claimed in claim 41, wherein the surfactant is a trihydroxy bile salt.

45. A method as claimed in claim 41, wherein the bile salt is selected from the salts of cholic, glycocholic and taurocholic acids.

46. A method as claimed in claim 41, wherein the bile salt is sodium taurocholate.

47. A method as claimed in claim 41, wherein the surfactant is a single-chain phospholipid.

48. A method as claimed in claim 41, wherein the surfactant is selected from alkyl glucosides and alkyl maltosides.

49. A method as claimed in claim 41, wherein the propellant comprises 1,1,1,2-tetrafluoroethane (P134a), 1,1,1,2,3,3,3-heptafluoropropane (P227) or 1,1-difluoroethane (P152a).

50. A method as claimed in claim 41, wherein the propellant comprises a density-matched mixture of 1,1,1,2-tetrafluoroethane (P134a) and 1,1,1,2,3,3,3-heptafluoropropane (P227).

51. A method as claimed in claim 41, wherein the polypeptide is of molecular weight up to 40 kD.

52. A method as claimed in claim 41, wherein the polypeptide is of molecular weight up to 20 kD.

53. A method as claimed in claim 41, wherein the polypeptide is of molecular weight up to 10 kD.

54. A method as claimed in claim 41, wherein the polypeptide is a peptide hormone.

55. A method as claimed in claim 41, wherein the polypeptide is selected from insulin, glucagon, C-peptide of insulin, vasopressin, desmopressin, corticotropin (ACTH), corticotropin releasing hormone (CRH), gonadotropin releasing hormone (GnRH), gonadotropin releasing hormone agonists and antagonists, gonadotropin, calcitonin, parathyroid hormone (PTH), bioactive fragments of PTH, growth hormone (GH), growth hormone releasing hormone (GHRH), somatostatin, oxytocin, atrial natriuretic factor (ANF), thyrotropin releasing hormone (TRH), deoxyribonuclease (DNase), prolactin, and follicle stimulating hormone (FSH), and biologically active analogues thereof.

56. A method as claimed in claim 41, wherein the polypeptide is insulin.

57. A method as claimed in claim 41, wherein the formulation further comprises ethanol in an amount of up to 20% by weight of propellant and surfactant.

58. A method as claimed in claim 41, wherein the formulation further comprises an additive selected from the group consisting of lactose, glucose, fructose, galactose, trehalose, sucrose, maltose, raffinose, maltitol, melezitose, stachyose, lactitol, palatinite, starch, xylitol, mannitol, myoinositol, a hydrate of any of the aforementioned carbohydrates, alanine, glycine, betaine, and albumen.

59. A method as claimed in claim 58, wherein the additive is melezitose.

60. A method as claimed in claim 41, wherein the surfactant is present in a surfactant:polypeptide ratio in the range of 1:10 to 1:0.2.

61. A method as claimed in claim 41, wherein at least 50% of the polypeptide is in the form of particles having a diameter of 0.01–10 microns.

62. A pharmaceutical aerosol formulation comprising (a) a HFA propellant; (b) a pharmaceutically active polypeptide dispersible in the propellant; and (c) a surfactant which is a $C_8$–$C_{16}$ fatty acid salt, a bile salt, a phospholipid, or an alkyl saccharide, wherein the surfactant enhances the systemic absorption of the polypeptide in the lower respiratory tract and the surfactant is dispersed in the propellant as solid particles.

63. A pharmaceutical aerosol formulation as claimed in claim 62, wherein the surfactant is a $C_8$–$C_{16}$ fatty acid salt.

64. A pharmaceutical aerosol formation as claimed in claim 63, wherein the fatty acid salt is selected from the sodium, potassium and lysine salts of caprylate ($C_8$), caprate ($C_{10}$), laurate ($C_{12}$) and myristate ($C_{14}$).

65. A pharmaceutical aerosol formulation as claimed in claim 62, wherein the surfactant is a trihydroxy bile salt.

66. A pharmaceutical aerosol formulation as claimed in claim 65, wherein the bile salt is selected from the salts of cholic, glycocholic and taurocholic acids.

67. A pharmaceutical aerosol formulation as claimed in claim 66, wherein the bile salt is selected from the sodium and potassium salts of cholic, glycocholic and taurocholic acids.

68. A pharmaceutical aerosol formulation as claimed in claim 67, wherein the bile salt is sodium taurocholate.

69. A pharmaceutical aerosol formulation as claimed in claim 62, wherein the surfactant is a single-chain phospholipid.

70. A pharmaceutical aerosol formulation as claimed in claim 69, wherein the surfactant is selected from lysophosphatidylcholines, lysophosphatidylglycerols, lysophosphatidylethanolamines, lysophosphatidylinositols and lysophosphatidylserines.

71. A pharmaceutical aerosol formulation as claimed in claim 62, wherein the surfactant is a double-chain phospholipid.

72. A pharmaceutical aerosol formulation as claimed in claim 62, wherein the surfactant is selected from the group consisting of diacylphosphatidylcholines, diacylphosphatidylglycerols, diacylphosphatidylethanolamines, diacylphosphatidylinositols and diacylphosphatidylserines.

73. A pharmaceutical aerosol formulation as claimed in claim 72, wherein the surfactant is selected from dioctanoylphosphatidylglycerol and dioctanoylphosphatidylcholine.

74. A pharmaceutical aerosol formulation as claimed in claim 72, wherein the surfactant is selected from alkyl glucosides and alkyl maltosides.

75. A pharmaceutical aerosol formulation as claimed in claim 74, wherein the surfactant is selected from decyl glucoside and dodecyl maltoside.

76. A pharmaceutical aerosol formulation as claimed in claim 62, wherein the propellant comprises 1,1,1,2-tetrafluoroethane (P134a); 1,1,1,2,3,3,3-heptafluoropropane (P227) or 1,1-difluoroethane (P152a).

77. A pharmaceutical aerosol formulation as claimed in claim 76, wherein the propellant comprises 1,1,1,2-tetrafluoroethane (P134a) and 1,1,1,2,3,3,3-heptafluoropropane (P227).

78. A pharmaceutical aerosol formulation as claimed in claim 77, wherein the propellant comprises a density-matched mixture of ,1,1,1,2-tetrafluoroethane (P134a) and 1,1,1,2,3,3,3-heptafluoropropane (P227).

79. A pharmaceutical aerosol formulation as claimed in claim 62, wherein the polypeptide is of molecular weight up to 40 kD.

80. A pharmaceutical aerosol formulation as claimed in claim 79, wherein the polypeptide is of molecular weight up to 30 kD.

81. A pharmaceutical aerosol formulation as claimed in claim 80, wherein the polypeptide is of molecular weight up to 25 kD.

82. A pharmaceutical aerosol formulation as claimed in claim 81, wherein the polypeptide is of molecular weight up to 15 kD.

83. A pharmaceutical aerosol formulation as claimed in claim 82, wherein the polypeptide is of molecular weight up to 10 kD.

84. A pharmaceutical aerosol formulation as claimed in claim 62, wherein the polypeptide is a peptide hormone.

85. A pharmaceutical aerosol formulation as claimed in claim 62, wherein the polypeptide is selected from the group consisting of glucagon, C-peptide of insulin, vasopressin, desmopressin, corticotropin (ACTH), corticotropin releasing hormone (CRH), gonadotropin releasing hormone (GnRH), gonadotropin releasing hormone agonists and antagonists, gonadotropin, calcitonin, parathyroid hormone (PTH), bioactive fragments of PTH, growth hormone (GH), growth hormone releasing hormone (GHRH), somatostatin, oxytocin, atrial natriuretic factor (ANF), thyrotropin releasing hormone (TRH), deoxyribonuclease (DNase), prolactin, and follicle stimulating hormone (FSH), and biologically active analogues thereof.

86. A pharmaceutical aerosol formulation as claimed in claim 62, wherein the polypeptide is insulin.

87. A pharmaceutical aerosol formulation as claimed in claim 62, including ethanol in an amount of up to 20% by weight of propellant and surfactant.

88. A pharmaceutical aerosol formulation as claimed in claim 62, including ethanol in an amount of up to 5% by weight of propellant and surfactant.

89. A pharmaceutical aerosol formulation as claimed in claim 62, additionally comprising an additive selected from the group consisting of adjuvants, carriers, flavouring agents, buffers, antioxidants and chemical stabilisers.

90. A pharmaceutical aerosol formulation as claimed in claim 89, wherein the additive is selected from the group consisting of lactose, glucose, fructose, galactose, trehalose, sucrose, maltose, raffinose, maltitol, melezitose, stachyose, lactitol, palatinite, starch, xylitol, mannitol, myoinositol, a hydrate of any of the aforementioned carbohydrates, alanine, glycine, betaine, and albumen.

91. A pharmaceutical aerosol formulation as claimed in claim 90, wherein the additive is melezitose.

92. A pharmaceutical aerosol formulation as claimed in claim 62, wherein the surfactant is present in a surfactant:polypeptide ratio in the range of 1:10 to 1:0.2.

93. A pharmaceutical aerosol formulation as claimed in claim 92, wherein the surfactant is present in a surfactant:polypeptide ratio in the range of 1:4 to 1:1.

94. A pharmaceutical aerosol formulation as claimed in claim 62, wherein at least 50% of the polypeptide consists of particles having a diameter of 0.01–10 microns.

95. A pharmaceutical aerosol formulation as claimed in claim 94, wherein at least 50% of the polypeptide consists of particles having a diameter of 0.1–6 microns.

96. A pharmaceutical aerosol formulation as claimed in claim 94, wherein at least 50% of the polypeptide consists of particles having a diameter of 0.1–5 microns.

97. A pharmaceutical aerosol formulation as claimed in claim 94, wherein at least 70% of the polypeptide consists of particles having a diameter of 0.01–10 microns.

98. A pharmaceutical aerosol formulation as claimed in claim 95, wherein at least 70% of the polypeptide consists of particles having a diameter of 0.1–6 microns.

99. A pharmaceutical aerosol formulation as claimed in claim 96, wherein at least 70% of the polypeptide consists of particles having a diameter of 0.1–5 microns.

100. A pharmaceutical aerosol formulation as claimed in claim 94, wherein at least 90% of the polypeptide consists of particles having a diameter of 0.01–10 microns.

101. A pharmaceutical aerosol formulation as claimed in claim 96, wherein at least 90% of the polypeptide consists of particles having a diameter of 0.1–5 microns.

102. A pharmaceutical aerosol formulation as claimed in claim 62, wherein the concentration of polypeptide is 0.1 mg/ml to 25 mg/ml of the formulation.

103. A method for the manufacture of a pharmaceutical aerosol formulation as claimed in claim 62, comprising the steps of: mixing the polypeptide and the surfactant in an aqueous buffer; drying to give a solid powder; and mixing the powder and the propellant in a vessel.

104. A method as claimed in claim 103, wherein said mixing step is carried out by first mixing a portion of the propellant with the powder in the vessel, and then adding the remaining propellant to the vessel.

105. A method for the treatment of a patient in need of therapy with a given polypeptide, comprising administering to said patient a therapeutically effective amount of the pharmaceutical aerosol formulation of claim 62, provided that the pharmaceutically active polypeptide in the formulation is said given polypeptide.

106. A method as claimed in claim 104, wherein the surfactant is a $C_8$–$C_{16}$ fatty acid salt.

107. A method as claimed in claim 104, wherein the fatty acid salt is selected from the sodium, potassium and lysine salts of caprylate ($C_8$), caprate ($C_{10}$), laurate ($C_{12}$) and myristate ($C_{14}$).

108. A method as claimed in claim 104, wherein the surfactant is a trihydroxy bile salt.

109. A method as claimed in claim 104, wherein the bile salt is selected from the salts of cholic, glycocholic and taurocholic acids.

110. A method as claimed in claim 104, wherein the bile salt is sodium taurocholate.

111. A method as claimed in claim 104, wherein the surfactant is a single-chain phospholipid.

112. A method as claimed in claim 104, wherein the surfactant is a double-chain phospholipid.

113. A method as claimed in claim 104, wherein the surfactant is selected from dioctanoylphosphatidylglycerol and dioctanoylphosphatidylcholine.

114. A method as claimed in claim 105, wherein the surfactant is selected from alkyl glucosides and alkyl maltosides.

115. A method as claimed in claim 105, wherein the propellant comprises 1,1,1,2-tetrafluoroethane (P134a), 1,1,1,2,3,3,3-heptafluoropropane (P227) or 1,1-difluoroethane (P152a).

116. A method as claimed in claim 105, wherein the propellant comprises a density-matched mixture of 1,1,1,2-tetrafluoroethane (P134a) and 1,1,1,2,3,3,3-heptafluoropropane (P227).

117. A method as claimed in claim 105, wherein the polypeptide is of molecular weight up to 40 kD.

118. A method as claimed in claim 105, wherein the polypeptide is of molecular weight up to 20 kD.

119. A method as claimed in claim 105, wherein the polypeptide is of molecular weight up to 10 kD.

120. A method as claimed in claim 105, wherein the polypeptide is a peptide hormone.

121. A method as claimed in claim 105, wherein the polypeptide is selected from glucagon, C-peptide of insulin, vasopressin, desmopressin, corticotropin (ACTH), corticotropin releasing hormone (CRH), gonadotropin releasing hormone (GnRH), gonadotropin releasing hormone agonists and antagonists, gonadotropin, calcitonin, parathyroid hormone (PTH), bioactive fragments of PTH, growth hormone (GH), growth hormone releasing hormone (GHRH), somatostatin, oxytocin, atrial natriuretic factor (ANF), thyrotropin releasing hormone (TRH), deoxyribonuclease (DNase), prolactin, and follicle stimulating hormone (FSH), and biologically active analogues thereof.

122. A method as claimed in claim 105, wherein the polypeptide is insulin.

123. A method as claimed in claim 105, wherein the formulation further comprises ethanol in an amount of up to 20% by weight of propellant and surfactant.

124. A method as claimed in claim 105, wherein the formulation further comprises an additive selected from the group consisting of lactose, glucose, fructose, galactose, trehalose, sucrose, maltose, raffinose, maltitol, melezitose, stachyose, lactitol, palatinite, starch, xylitol, mannitol, myoinositol, a hydrate of any of the aforementioned carbohydrates, alanine, glycine, betaine, and albumen.

125. A method as claimed in claim 124, wherein the additive is melezitose.

126. A method as claimed in claim 105, wherein the surfactant is present in a surfactant:polypeptide ratio in the range of 1:10 to 1:0.2.

127. A method as claimed in claim 105, wherein at least 50% of the polypeptide is in the form of particles having a diameter of 0.01–10 microns.

* * * * *

UNITED STATES PATENT AND TRADEMARK OFFICE

CERTIFICATE OF CORRECTION

PATENT NO. : 6,524,557 B1 Page 1 of 1
DATED : February 25, 2003
INVENTOR(S) : Elisabet Lindgvist et al.

It is certified that error appears in the above-identified patent and that said Letters Patent is hereby corrected as shown below:

<u>Title page,</u>
Item [22], delete "Dec. 19, 1994" and insert -- Dec. 19, 1995 --.
Item [86], delete "April 4, 1996" and insert -- April 5, 1996 --.
Item [56], References Cited, U.S. PATENT DOCUMENTS, delete

| | | |
|---|---|---|
| "4,788,221 | A 11/1988 | Kagati" and insert |
| -- 4,788,221 | A 11/1988 | Kagatani --; and delete |
| "5,364,838 | A 11/1994 | Rudsamen" and insert |
| -- 5,364,838 | A 11/1994 | Rubsamen --; and delete |
| "5,506,203 | A 4/1996 | Backstrom" and insert |
| -- 5,506,203 | A 4/1996 | Bäckström et al. --; and delete |
| "5,830,853 | A 11/1998 | Bäström" and insert |
| -- 5,830,853 | A 11/1998 | Bäckström --; and delete |
| "GB 837465 | 6/1915" and insert | |
| -- GB 837465 | 6/1950 --. | |

Signed and Sealed this

Twenty-seventh Day of September, 2005

JON W. DUDAS
*Director of the United States Patent and Trademark Office*